United States Patent [19]

Yoon

[11] Patent Number: 5,451,204
[45] Date of Patent: Sep. 19, 1995

[54] MULTIFUNCTIONAL DEVICES FOR ENDOSCOPIC SURGICAL PROCEDURES

[76] Inventor: InBae Yoon, 2101 Highland Ridge Dr., Phoenix, Md. 21131

[21] Appl. No.: 45,768

[22] Filed: Apr. 14, 1993

Related U.S. Application Data

[60] Continuation-in-part of Ser. No. 789,599, Nov. 8, 1991, abandoned, which is a division of Ser. No. 556,081, Jul. 24, 1990, Pat. No. 5,074,840, Ser. No. 600,775, Oct. 23, 1990, Pat. No. 5,374,261, and Ser. No. 596,937, Oct. 15, 1990, which is a continuation-in-part of Ser. No. 222,776, Jul. 22, 1988, abandoned, said Ser. No. 600,775, is a continuation-in-part of Ser. No. 556,081, Jul. 24, 1990.

[51] Int. Cl.⁶ ............................................. A61M 35/00
[52] U.S. Cl. ......................................... 604/1; 128/759
[58] Field of Search ................. 604/1, 15; 600/29, 30; 128/766, 759

[56] References Cited

U.S. PATENT DOCUMENTS

| | | |
|---|---|---|
| 654,564 | 7/1900 | Dargatz . |
| 682,090 | 9/1901 | Lee . |
| 702,997 | 6/1902 | Pugh . |
| 716,040 | 12/1902 | Holt . |
| 1,523,943 | 1/1925 | Fowle . |
| 1,562,656 | 11/1925 | Park . |
| 2,524,195 | 10/1950 | Hoover . |
| 3,039,468 | 6/1962 | Price . |
| 3,095,877 | 7/1963 | Rowan . |
| 3,253,594 | 5/1966 | Matthews et al. . |
| 3,459,175 | 8/1969 | Miller . |
| 3,495,586 | 2/1970 | Regenbogen . |
| 3,557,794 | 1/1971 | Van Patten . |
| 3,683,915 | 8/1972 | Voss . |
| 3,790,433 | 2/1974 | Baron . |
| 3,833,003 | 9/1974 | Taricco . |
| 3,941,125 | 3/1976 | Drake . |
| 3,952,742 | 4/1976 | Taylor . |
| 4,019,499 | 4/1977 | Fitzgerald ............................. 600/30 |
| 4,027,673 | 6/1977 | Poncy et al. . |
| 4,043,338 | 8/1977 | Homm et al. . |
| 4,077,412 | 3/1978 | Moossun . |
| 4,192,300 | 3/1980 | Devers . |
| 4,328,804 | 5/1982 | Shimatani . |
| 4,335,720 | 6/1982 | Glassman . |
| 4,372,295 | 2/1983 | Heckele . |
| 4,421,504 | 12/1983 | Kline . |
| 4,535,773 | 8/1985 | Yoon . |
| 4,553,965 | 11/1985 | Conn et al. . |
| 4,573,964 | 3/1986 | Huffman . |
| 4,607,619 | 8/1986 | Seike et al. . |
| 4,608,965 | 9/1986 | Anspach, Jr. et al. . |
| 4,610,659 | 9/1986 | Friese . |
| 4,748,982 | 6/1988 | Horzewski et al. . |
| 4,822,332 | 4/1989 | Kajander . |
| 4,857,044 | 8/1989 | Lennon . |
| 4,895,559 | 1/1990 | Shippert . |
| 4,900,315 | 2/1990 | Lundqvist et al. . |
| 5,002,557 | 3/1991 | Hasson . |
| 5,007,895 | 4/1991 | Burnett . |
| 5,041,093 | 8/1991 | Chu . |
| 5,074,840 | 12/1991 | Yoon . |
| 5,074,871 | 12/1991 | Groshong . |
| 5,113,846 | 5/1992 | Hiltebrandt et al. . |
| 5,232,444 | 8/1993 | Just et al. ................................ 604/96 |

FOREIGN PATENT DOCUMENTS

| | | |
|---|---|---|
| 0278937 | 8/1988 | European Pat. Off. . |
| 0432363 | 6/1991 | European Pat. Off. . |
| 3519626 | 12/1986 | Germany ............................. 606/159 |

Primary Examiner—Jerome L. Kruter

[57] ABSTRACT

A multifunctional device for insertion in an anatomical cavity through a narrow portal includes an expandable bladder, a body of fluid absorbing material carried by the bladder and a mechanism, which can be inflation or mechanical, for expanding the bladder. The device has a cross-sectional size in a compressed state with the fluid absorbing material in a dry state and the bladder contracted to facilitate insertion of the device through the portal. The fluid absorbing material is soft and expandable in a wet state upon absorption of body fluids in the anatomical cavity, and the bladder is movable via the expanding mechanism to move the device to an expanded state wherein the cross-sectional size of the device is increased. The bladder is movable to decrease the size of the device to facilitate withdrawal of the device from the anatomical cavity through the portal.

10 Claims, 5 Drawing Sheets

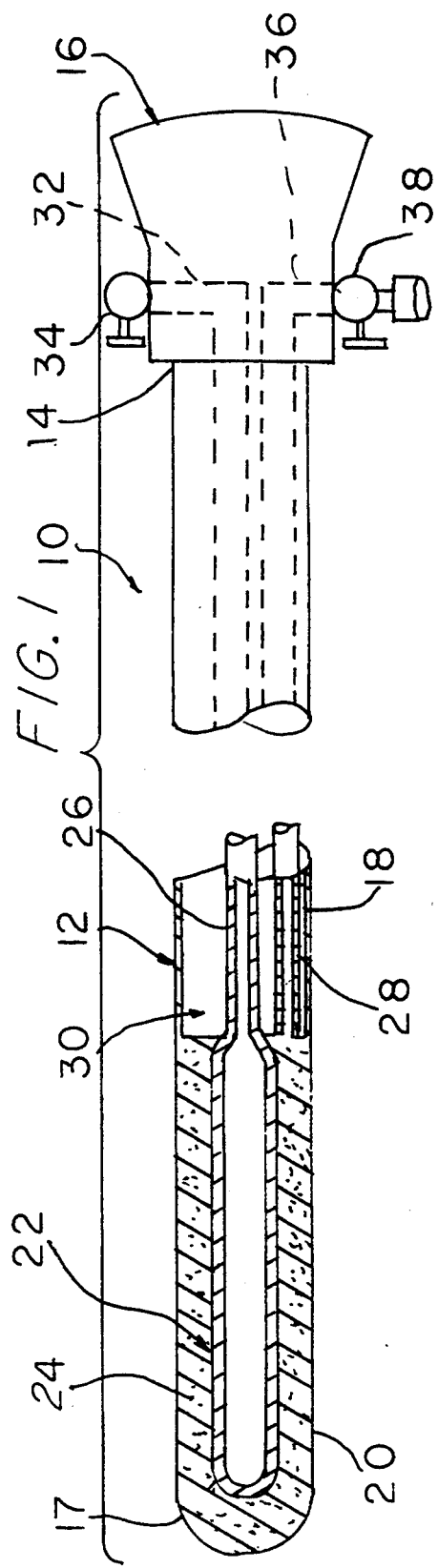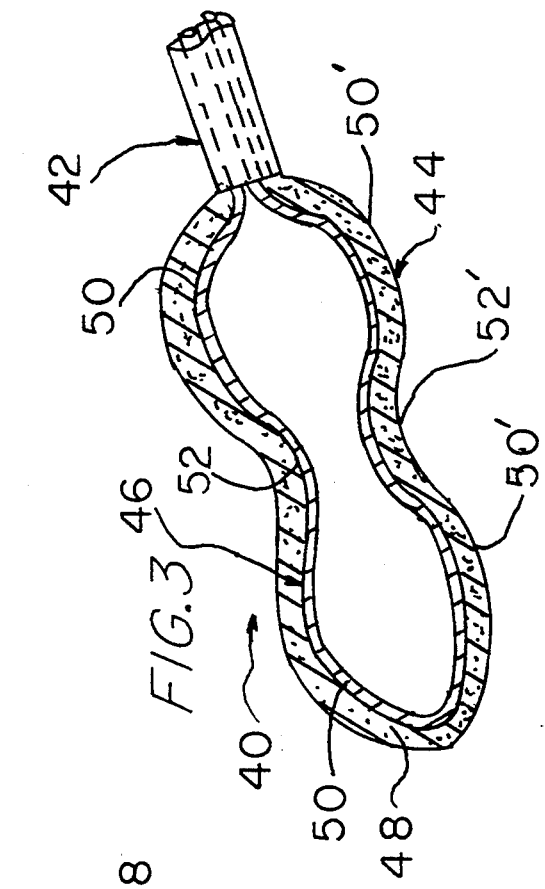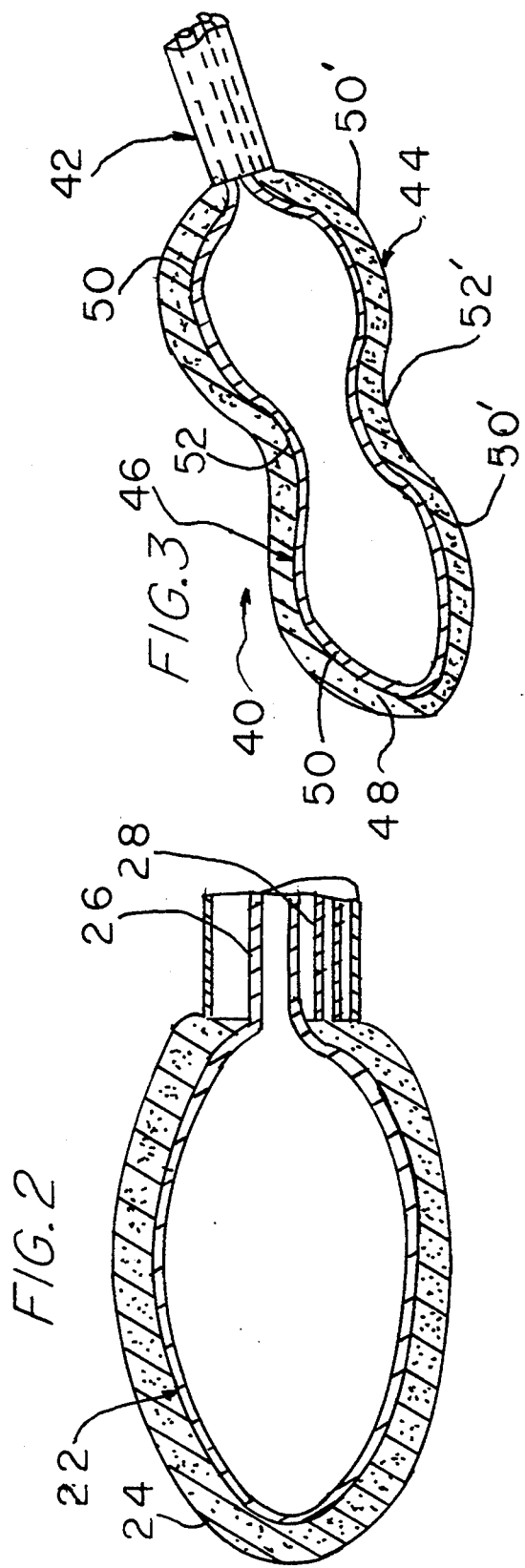

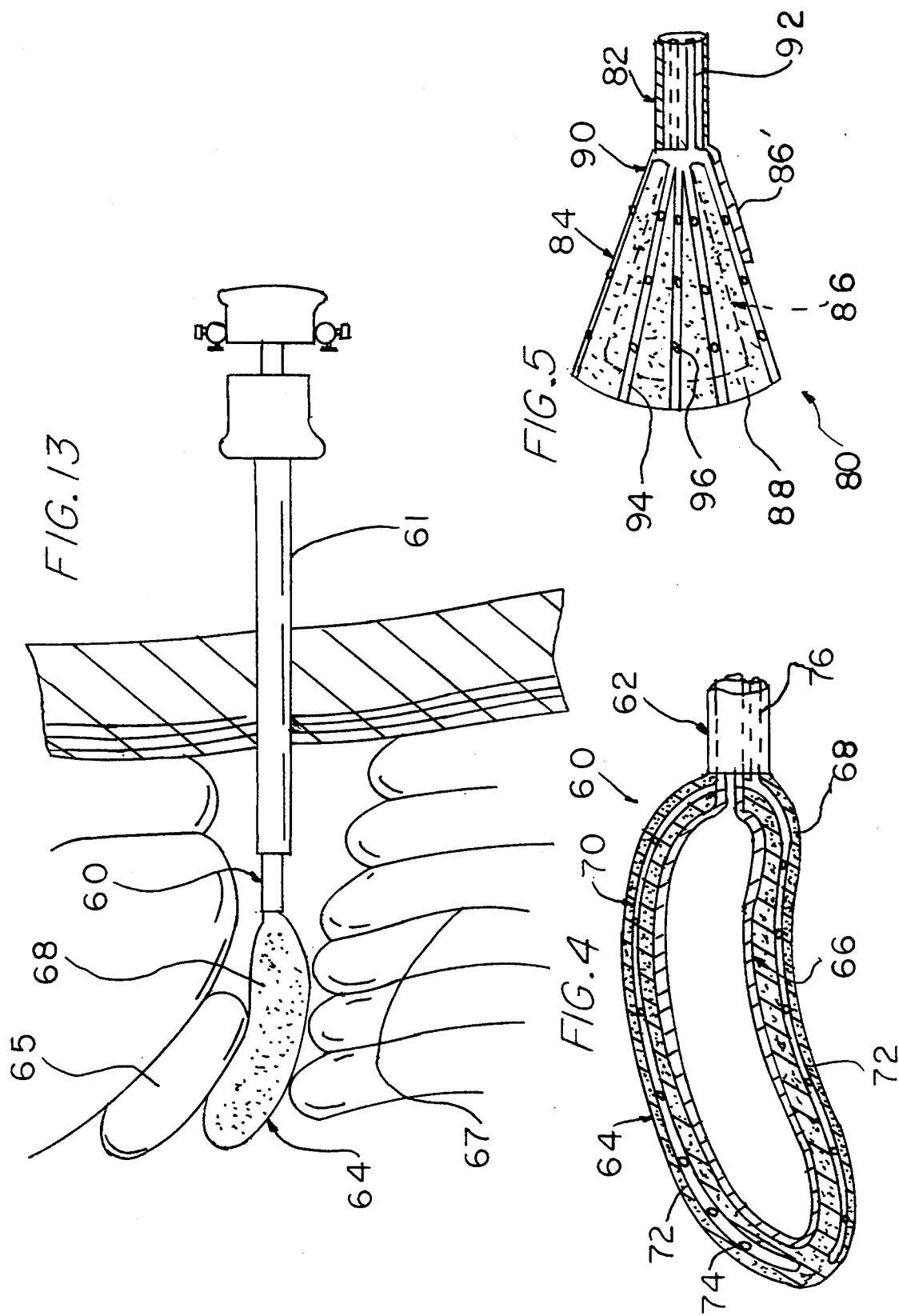

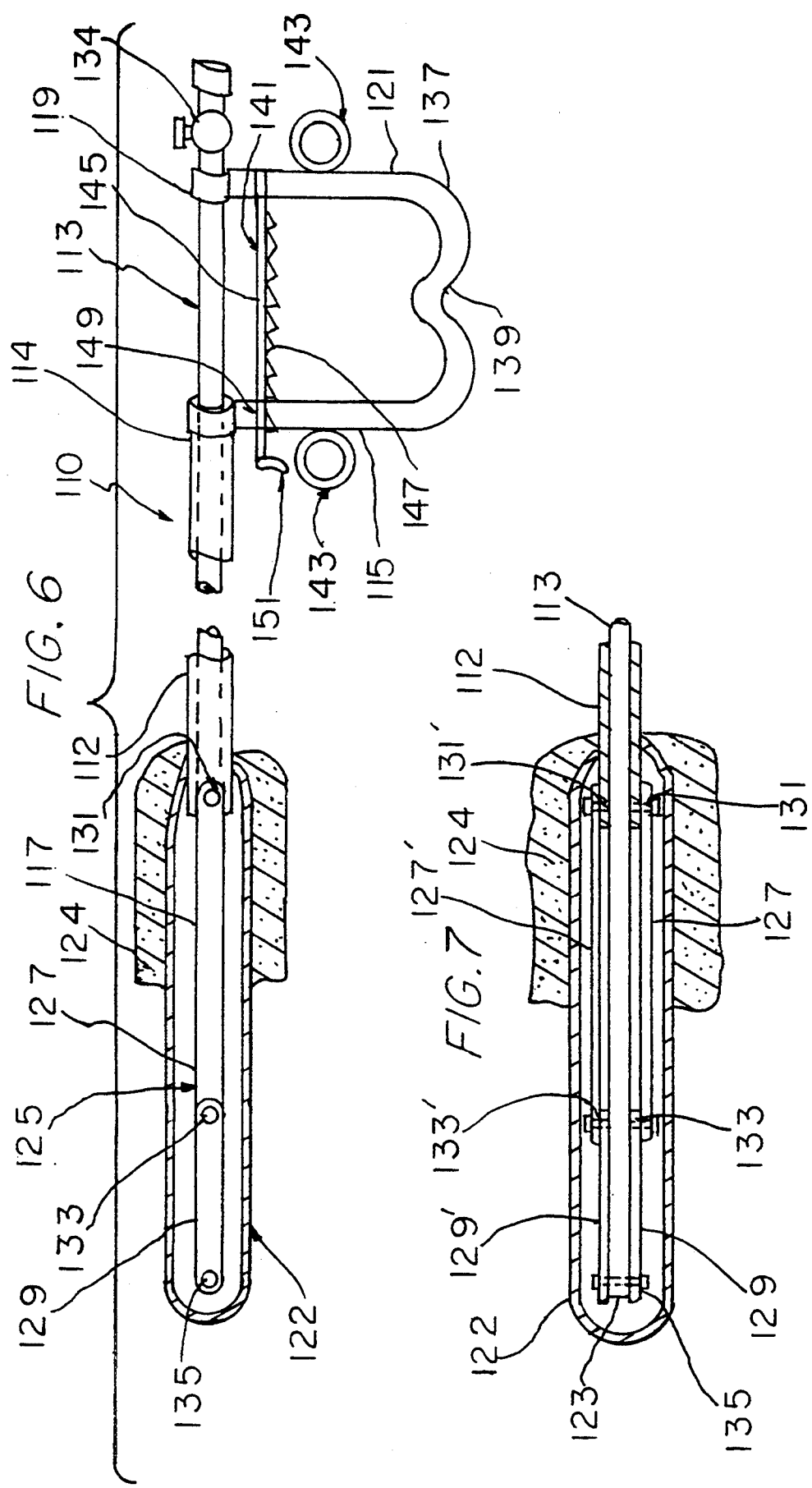

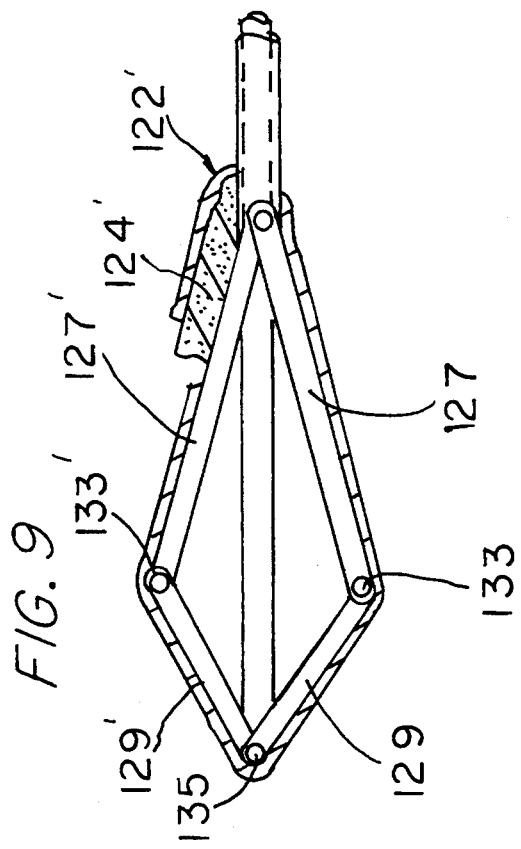
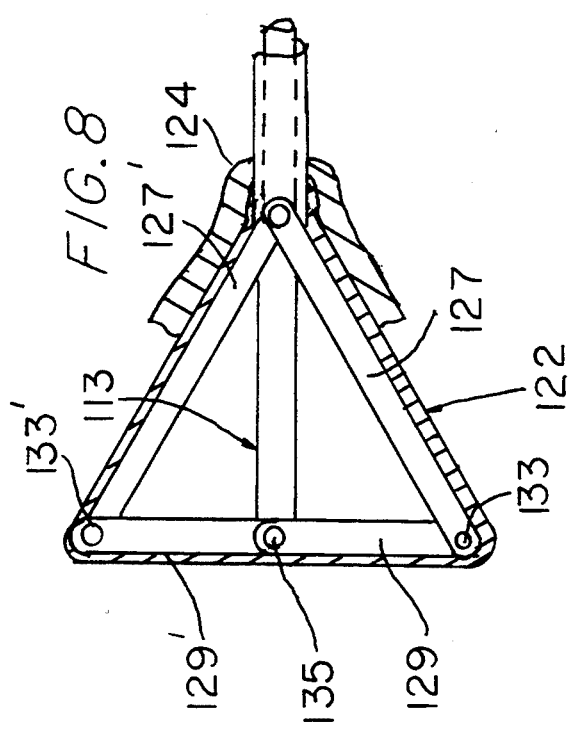
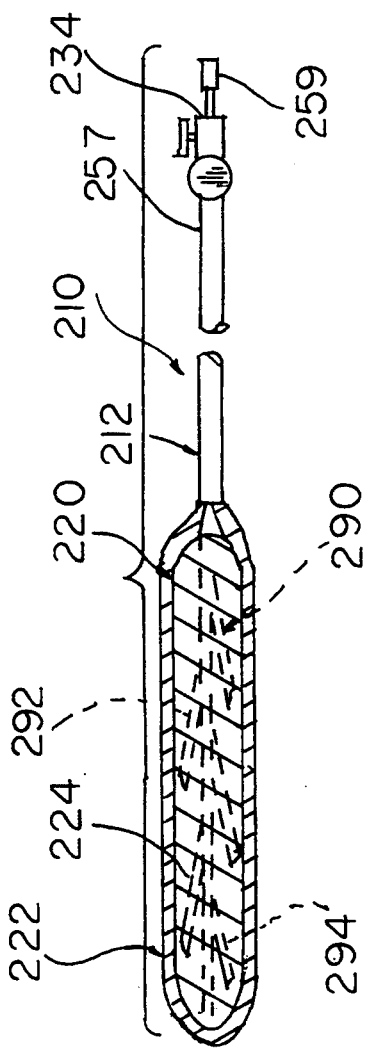

MULTIFUNCTIONAL DEVICES FOR ENDOSCOPIC SURGICAL PROCEDURES

CROSS-REFERENCE TO RELATED PATENT APPLICATIONS

This application is a continuation-in-part of patent application Ser. No. 07/789,599, filed Nov. 8, 1991, now abandoned which is a division of patent application Ser. No. 07/556,081, filed Jul. 24, 1990, now U.S. Pat. No. 5,074,840, patent application Ser. No. 07/600,775, filed Oct. 23, 1990 now U.S. Pat. No. 5,374,261, which is a continuation-in-part of patent application Ser. No. 07/556,081 now U.S. Pat. No. 5,074,840, and patent application Ser. No. 07/596,937, filed Oct. 15, 1990 abandoned, which is a continuation-in-part of patent application Ser. No. 222,776, filed Jul. 22, 1988, now abandoned. The above patent applications are incorporated herein by reference.

BACKGROUDN OF THE IVNENTION

1. Field of the Invention

The present invention relates to endoscopic surgery and, more particularly, to devices and methods for use in endoscopic surgery to absorb body fluids, manipulate or retract tissue or organ structures, separate adhering tissue (lysis of adhesion), and/or pack the endoscopic surgical site to isolate tissue to be treated, protect surrounding tissue and increase visibility for the surgeon.

2. Description of the Prior Art

Endoscopically performed operative procedures are preferred for surgery on the human body due to their least invasive nature and reduced trauma and tissue damage as compared with open surgery. While endoscopically performed operative procedures are preferred, there are and have been obstacles to expanding endoscopy to include the various procedures currently performed with open surgery. For example, prior to applicant's patent applications Ser. Nos. 07/556,081, now U.S. Pat. No. 5,074,840, 07/600,775 and 07/789,599, the specifications of which are incorporated herein by reference, packing of the internal operative site could not be accomplished. Without packing, endoscopic procedures are much more difficult and dangerous to perform since the tissue or organ structure can not be adequately exposed and manipulated, the surrounding tissue and organ structure is not protected during the procedure and body fluids cannot be removed from the operative site without the use of expensive and cumbersome suction equipment. Furthermore, electrosurgical or laser instruments as commonly used in endoscopic procedures for coagulation and cutting present the opportunity for accidental contact or scarring of tissue not intended to be treated if the operative site is not adequately packed to expose and isolate the tissue to be treated and if vision is impaired by blood or other body fluids. Accordingly, great care is required when utilizing laser and electrosurgical probes to assure that adjacent tissue is not inadvertently damaged thusly increasing the time required to complete the surgery. Additionally, in most endoscopic procedures, there is very little space at the operative site in which to introduce and maneuver instruments such that facilitating procedures including, for example, tissue retraction and manipulation, cleaning and wiping of tissue, lysis of adhesion and irrigation and/or aspiration, cannot be achieved.

Applicant's patent applications referenced above disclose multifunctional devices for being introduced at an internal operative site, such as an operative site within an anatomical cavity, through a narrow portal, such as a natural or incisional opening or a portal sleeve, to perform or facilitate various procedures including, for example, manipulation or retraction of tissue or organ structure, irrigation, absorption of body fluids, separation of adhering tissue and/or packing of an endoscopic operative site to isolate tissue to be treated, protect surrounding tissue and increase visibility for the surgeon. It is desirable in many procedures, such as cystic cavity coagulation, endometrial ablation and uterine manipulation, for example, in which the multifunctional devices are utilized for the devices to have a relatively large external size or surface area for increased exposure to tissue. Accordingly, there is a need to allow the external size or surface area of the multifunctional devices to be selectively increased during use to enhance various procedures and, in particular, to increase the external size or surface area of multifunctional devices utilizing an absorbent material while minimizing the quantity of absorbent material required. There is also a need to facilitate reducing or decreasing the external size or surface area of the multifunctional devices to facilitate withdrawal of the devices through the portal.

SUMMARY OF THE INVENTION

Accordingly, it is a primary object of the present invention to improve the efficacy and safety of endoscopic operative procedures.

Another object of the present invention is to provide a multifunctional device of a size to be introduced at and withdrawn from an operative site in an anatomical cavity via a narrow portal, such as a portal sleeve, while being expandable at the operative site to perform various functions, such as absorption of body fluids, manipulation of tissue, lysis of adhesion, irrigation, aspiration and packing.

A further object of the present invention is to expand and contract a device for absorbing body fluids in an anatomical cavity during endoscopic surgery by inflation and deflation and/or mechanically.

An additional object of the present invention is to utilize an expandable bladder in combination with an expanding mechanism to facilitate use, introduction and withdrawal of a fluid absorbing device in endoscopic operative procedures.

It is also an object of the present invention to provide a multifunctional device having an absorbent material arranged within an expandable bladder to enhance the safety of endoscopic operative procedures in the event that the bladder ruptures.

Yet another object of the present invention is to allow the external size or surface area of a multifunctional device to be selectively increased for increased exposure to tissue by utilizing an expandable bladder.

Still a further object of the present invention is to increase the potential external size or surface area of a multifunctional device including an absorbent material while minimizing the quantity of absorbent material required through the use of an expandable bladder surrounded by the absorbent material.

The present invention has as an additional object to allow the external size or surface area of a multifunctional device to be selectively varied during use at an internal operative site by employing a selectively expandable bladder.

Some of the advantages of the present invention include improved visibility in endoscopic procedures, reduced need for insufflation in laparoscopy, precise packing at an internal operative site can be accomplished via a narrow portal, use of the multifunctional devices provides improved exposure of the operative site, protects surrounding tissue and organ structure, allows irrigation and/or aspiration or drainage with a cleansing effect and the multifunctional devices according to the present invention are sufficiently rigid in a non-expanded or contracted state to allow precise placement thereof as well as manipulation of tissue, facilitate removal of infected fluids and abnormal fluids, can serve as a culturing medium, can be used to apply medicaments to tissue, can contain specific medications for specific medical purposes or radiopaque materials for identification or location purposes, can be individually identified externally and can serve as an indicator for possible damage to healthy tissue from inadvertent contact with electrosurgical probes.

These and other objects, advantages and benefits are realized with the present invention as characterized in a multifunctional device for insertion in an anatomical cavity through a narrow or endoscopic portal and including an expandable bladder or membrane and a body of fluid absorbing material carried, externally or internally, by the bladder with the bladder being movable, mechanically or via inflation with fluids, between a contracted state wherein the device has a cross-sectional size facilitating passage through the portal and an expanded state wherein the cross-sectional size of the device is increased within the anatomical cavity. The fluid absorbing material has a configuration and stiffness in a dry state to facilitate insertion through the portal and a soft, expanded configuration in a wet state upon absorption of body fluids in the anatomical cavity. The bladder can be inflated with air or saline supplied to the interior thereof or expanded mechanically with the use of various spines, expanding mechanisms or due to expansion of the fluid absorbing material where the material is arranged within the bladder. The bladder can be constructed to have a predetermined configuration in the expanded state upon inflation with fluid, or the fluid absorbing material, spines and expanding mechanisms can be utilized to obtain a predetermined configuration for the device in the expanded state. Expansion of the device can be selectively controlled such that the expanded size as well as the configuration of the device can be varied during use. The spines and expanding mechanisms can be arranged externally or internally of the bladder and externally of, internally of or within the fluid absorbing material.

Other objects and advantages of the present invention will become apparent from the following description of the preferred embodiments taken in conjunction with the accompanying drawings wherein like parts in each of the several figures are identified by the same reference characters.

BRIEF DESCRIPTION OF THE DRAWINGS

FIG. 1 is a broken side view, partly in section, of a multifunctional device according to the present invention in a contracted state.

FIG. 2 is a broken, side sectional view of the multifunctional device of FIG. 1 in an expanded state.

FIG. 3 is a broken side view, partly in section, of a modification of the multifunctional device according to the present invention having a segmented configuration in the expanded state.

FIG. 4 is a broken side view, partly in section, of a further modification of a multifunctional device according to the present invention having a curved configuration in the expanded state.

FIG. 5 is a broken side view, partly in section, of an additional modification of a multifunctional device according to the present invention having a conical shape in the expanded state.

FIG. 6 is a broken side view, partly in section, of a further modification of the multifunctional device according to the present invention in the contracted state.

FIG. 7 is a broken top view, partly in section, of the multifunctional device of FIG. 6.

FIG. 8 is a broken side view, partly in section, of the multifunctional device of FIG. 6 in a first expanded state.

FIG. 9 is a broken side view, partly in section, of the multifunctional device of FIG. 6 in a second expanded state.

FIG. 10 is a broken top view of the expanding mechanism for the multifunctional device of FIG. 6.

FIG. 11 is a broken side view, partly in section, of yet another modification of the multifunctional device according to the present invention.

FIGS. 12 and 13 are exploded, broken views, partly in section, illustrating use of the multifunctional device of FIG. 4.

DESCRIPTION OF THE PREFERRED EMBODIMENTS

Figure 12:
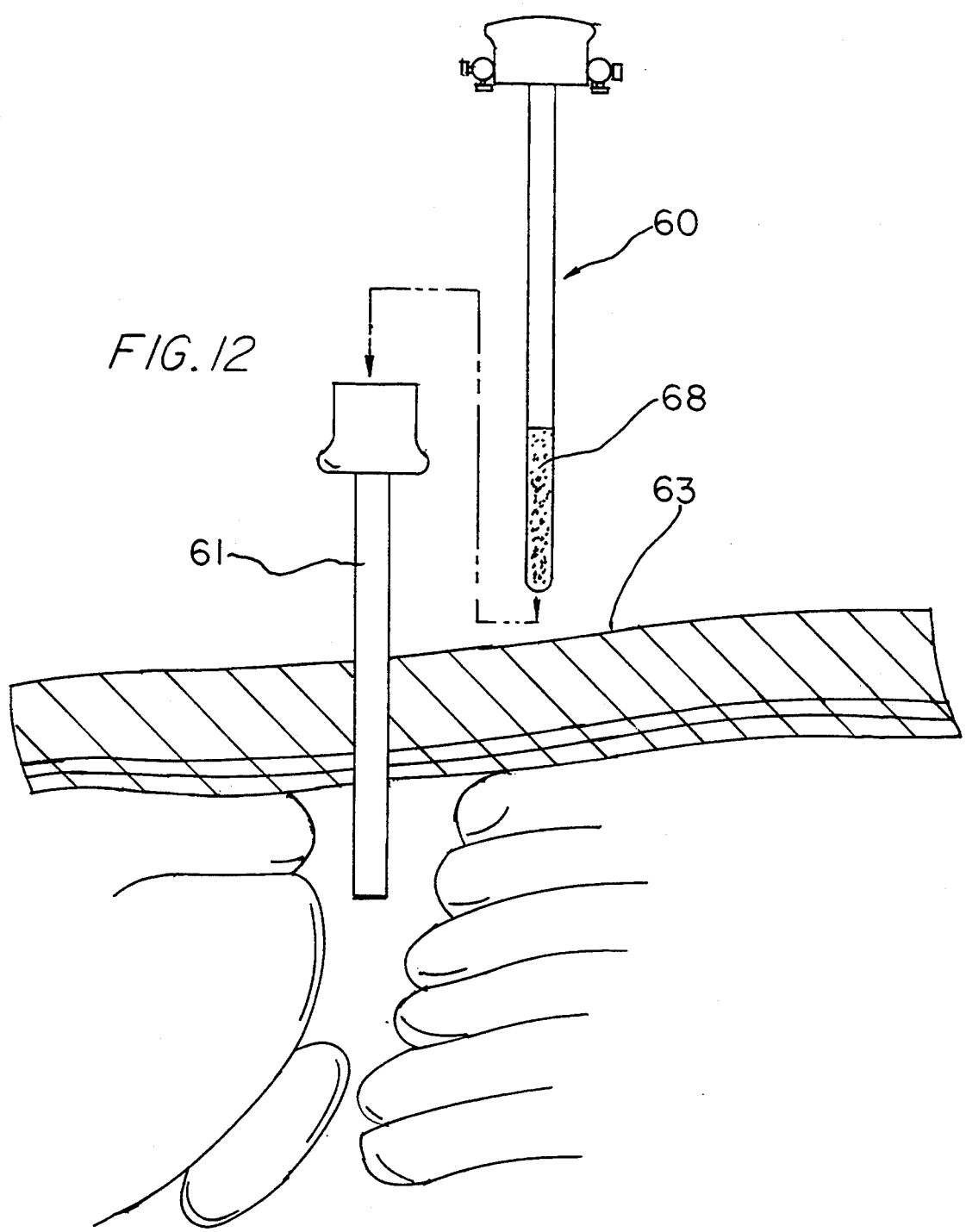

A multifunctional device in accordance with the present invention is illustrated at 10 in FIG. 1. The multifunctional device 10 can be introduced at an internal operative site, typically within an anatomical cavity, through any type of narrow portal, including a narrow incisional or natural entry opening, or a portal sleeve, cannula, or the operating channel of an endoscope, for example, communicating with the operative site as shown and described in applicant's patent applications Ser. Nos. 07/556,081, 07/596,937, 07/600,775 and 07/789,599, the specifications of which are incorporated herein by reference. The multifunctional device 10 is formed of an elongate member 12 having a proximal end 14 mounted to a housing 16 and a distal end 17. Elongate member 12 is made up of a proximal portion or segment 18 and a distal portion or segment 20 joined to proximal portion 18. Proximal portion 18 can be made of a length of rigid, substantially rigid, semi-rigid or flexible medical grade material, such as metal or plastic, suitable to be inserted in the body. Distal portion 20 is made up of a bladder 22 and a body or layer of absorbent material 24 carried by the bladder 22. Absorbent material 24 can be any type of medical grade material that is relatively rigid or stiff in a dry state for introduction at the operative site through the portal and that can absorb body fluids to be soft, pliant and expandable in a wet state. Depending on the configuration of the portal and the procedure to be performed, the distal portion 20 can have some flexibility in the dry state. As illustrated in FIG. 1, distal portion 20 has a cylindrical, rod-like, substantially straight configuration in the dry state. In the dry state, the material 24 should be sufficiently rigid to allow the multifunctional device to be manipulated at the operative site to expose and isolate as well as contact and move or position tissue or organ structures to facilitate the operative procedure to be performed. In the wet state, the material 24 should be soft enough to bend freely and repeatedly without breaking and be malleable and flexible as well as expandable to an external size or surface area larger than the external size or surface area in the dry state. One preferred material for material 24 is a sponge material including, for example, compressed cellulose sponge, natural sponge, synthetic sponge and polyurethane foam. The length and width or lateral size of the elongate member 12 will depend upon the procedure to be performed and the size of the portal. The proximal and distal portions can both be cylindrical, as shown, or have any other desired configuration in cross-section, and the proximal and distal portions can have the same or different cross-sectional configurations. The outer diameter, width or lateral size of proximal portion 18 can be the same or substantially the same as the outer diameter, width or lateral size of distal portion 20 as shown, or the proximal and distal portions can have different diameters, widths or lateral sizes. If desired, proximal portion 18 can be made integrally, unitarily with distal portion 20 of absorbent material 24 or the proximal and distal portions can be made separately and/or of different materials. Where proximal portion 18 is made separately from distal portion 20, the distal portion can be secured to the proximal portion in many various ways, such as adhesively, depending on the materials utilized.

Bladder 22 is made of an expandable, stretchable or elastic material or membrane such as rubber, Tecoflex EG-85A made by Thermedics, Inc., Goretex and Teflon, for example. Bladder 22 is surrounded by the absorbent material 24, the absorbent material being arranged as a layer secured to an external surface of the bladder to move with the bladder from a contracted, compressed or non-expanded state or position wherein the bladder is disposed close to a longitudinal axis of device 10 as illustrated in FIG. 1 to an expanded state wherein the bladder is disposed away from the axis as illustrated in FIG. 2. Bladder 22 defines an envelope within multifunctional device 10 for being supplied with a material, such as fluids including air or saline, for example, to expand or inflate the bladder, or the bladder can be expanded mechanically with a spine or an expanding mechanism as will be explained further below. A tube 26 made of non-expandable material is connected with bladder 22 to communicate with the interior thereof for supplying material to expand the bladder; and, if desired, a tube 28 can be connected with absorbent material 24 for supplying medicaments or other therapeutic or irrigating substances or for draining fluids through material 24. The portion of elongate member 12 through which tubes 26 and 28 extend is formed with a single interior passage or separate interior passages for receiving the tubes therethrough. As shown in FIG. 1, tubes 26 and 28 extend through proximal portion 18, and the proximal portion is made tubular with a lumen 30 allowing passage therethrough by the tubes.

Housing 16 can be made of any suitable material to be disposable or reusable with a forward end to permanently or releasably mount elongate member 12. Elongate member 12 can be secured to housing 16 in many various ways, such as adhesively or with the use of any suitable mechanical detents or mechanisms, for example. Housing 16 can have any desirable configuration in cross-section; and, as illustrated in FIG. 1, housing 16 is cylindrical in configuration with an outwardly flared rearward end to facilitate grasping by a surgeon. A transverse proximal portion 32 of tube 26 extends through housing 16 and is coupled with a stop cock 34 or other valve mounted externally along the housing for being connected with a source of material to be supplied to bladder 22. A transverse proximal portion 36 of tube 28 extends through housing 16 in a direction opposite the direction of portion 32 and is coupled with a stop cock 38 or other valve mounted externally along the housing 16 for being connected with a source of medicaments or other therapeutic substances or irrigating fluids to be introduced at the operative site or suction for selective or continuous drainage or aspiration of fluids from the operative site. Tubes 26 and 28 can be coupled with valves 34 and 38, respectively, in many various ways depending on the way in which elongate member 12 is secured to housing 16. Valves 34 and 38 can be arranged in many various ways to be conveniently operated by the hand of the surgeon grasping housing 16, and the valves can be mounted externally of the housing wholly or partially or internally. As illustrated in FIG. 1, valves 34 and 38 are disposed on opposite sides of housing 16 for bilateral operation. It will be appreciated that the same valve utilized to supply material to expand the bladder 22, i.e. valve 34 in FIG. 1, can be utilized to withdraw, remove or release material from the bladder to control and/or vary the external or cross-sectional size of the distal portion 20 in the expanded state as will be explained further below or a different valve can be provided for withdrawing material from the bladder.

In use, multifunctional device 10 in the non-expanded, compressed or contracted state with material 24 in the dry state is inserted at an internal operative site, such as an operative site within an anatomical cavity, through a relatively narrow portal, such as a portal sleeve positioned through a wall of the anatomical cavity, to position distal portion 20 at the operative site with housing 16 held externally of the anatomical cavity. The stiffness or rigidity and rod-like configuration of material 24 in the dry state allows the elongate member 12 to be introduced through the portal sleeve in a straight or linear path and distal portion 20 to be positioned via manipulation of housing 16 to expose and isolate tissue or organ structures to be treated and/or to manipulate, retract or position the tissue or organ structures. Once the distal portion 20 is in the body, material 24 will absorb body fluids to become soft and will expand in the wet state. Once material 24 is in the wet state, air or saline is supplied to the interior of bladder 22 via valve 34 and tube 26 to inflate or expand the bladder. The multifunctional device 10 is shown in FIG. 2 with bladder 22 filled with fluid in the expanded state, and the external size or surface area of the distal portion 20 in the expanded state can be selectively controlled by controlling the amount of fluid supplied to the bladder. In the expanded state, multifunctional device 10 has an external cross-sectional size or surface area substantially larger than the external cross-sectional size or surface area in the contracted state, and the external size or surface area in the expanded state can be much greater than that of the device in the wet state. In the expanded state, the multifunctional device 10 can be utilized to perform or facilitate many various functions, including, for example, manipulation, retraction or positioning of tissue or organ structures, separation of adhering tissue (lysis of adhesion), packing of the endoscopic surgical site to isolate tissue to be treated, protecting tissue adjacent to tissue to be treated and increasing visibility for the surgeon. Material 24 can be utilized to absorb body fluids for continuous or selective drainage through tube 28, and a source of suction can be connected with valve 38 to facilitate drainage or aspiration. A source of medicaments or other therapeutic substances or irrigating fluids can be connected with valve 38 for introduction in the anatomical cavity through tube 28 and material 24. The device 10 facilitates simultaneous manipulation of tissue, cleaning and wiping of tissue, and aspiration and/or irrigation at the operative site to increase visualization and facilitate precise positioning and use of instruments employed in the operative procedure. When it is desired to withdraw multifunctional device 10 from the operative site, fluid is released from bladder 22 via valve 34 to collapse or contract the bladder allowing withdrawal through the portal, and withdrawal of the device can be further facilitated by removing fluid from material 24 via suction through tube 28.

The multifunctional device 10 can be utilized with the various spines and in the various procedures disclosed in applicant's previous patent applications incorporated herein by reference. Material 24 can be designed as disclosed in applicant's previous patent applications to have shape memory characteristics causing the material to assume a predetermined configuration in the wet state with bladder 22 conforming to the configuration of material 24. By varying or gradually varying the density, wall thickness or strength of bladder 22 such that some portions of the bladder are more resistant to expansion than other portions, a predetermined configuration in the expanded state can be obtained for multifunctional device 10 without the need for a spine or shape molding of material 24. The multifunctional device 10 can have in the expanded state the various predetermined external configurations shown in applicant's prior patent applications, and the external configurations can be achieved through the use of a spine or other mechanical expanding mechanism, shape molding of material 24 or by varying the density or wall thickness of bladder 22, for example. Where obtained through use of a spine or shape molding of material 24, the predetermined external configuration can be obtained automatically upon absorption of fluids by material 24 and can thereafter be selectively increased in size through expansion of bladder 22. Where obtained by varying the density or strength of bladder 22, the predetermined external configuration and a desirable size therefore can be obtained selectively through expansion of the bladder with fluid supplied to the interior thereof. Material 24 can be surrounded by an elastic, stretchable membrane with or without apertures therein allowing material 24 to be a non-medically accepted material. Material 24 can be disposed externally of the bladder or within the bladder. By arranging material 24 externally of bladder 22, the device is particularly useful for separating adhering tissue (lysis of adhesion), such as uterine adhesions. Various probes such as electrosurgical, laser, biopsy, culturing, and needles, for example, can be introduced at the operative site through elongate member 12, and the probes can be introduced through the material 24, a spine, or laterally offset from bladder 22. Where electrosurgical or other instruments are introduced at the anatomical cavity, rupture of the bladder due to contact of the device by the instruments serves as an indicator that the instruments may have inadvertently gone astray allowing the surgeon to examine the surrounding tissue for possible injury by the instruments.

A modification of a multifunctional device in accordance with the present invention is illustrated in FIG. 3 at 40. Multifunctional device 40 is similar to multifunctional device 10 and includes elongate member 42 having a distal portion 44 made up of a bladder 46 and a body of absorbent material 48 carried by bladder 46. Bladder 46 is formed of alternating segments 50 and 52 with segments 52 having a density, strength or wall thickness substantially greater than the density, strength or wall thickness of segments 50 such that segments 52 are more resistant to stretching or expansion than segments 50. The distal portion 44 can have a cylindrical, rod-like configuration in the contracted state similar to the configuration of distal portion 20 in FIG. 1; and, after introduction into the body and absorption of fluid by material 48, bladder 46 can be expanded with fluid supplied to the interior thereof. In the expanded state, distal portion 44 will have a plurality of protuberant segments defining spherical protuberances 50' interconnected by smaller segments 52', segments 52 not expanding to the same size as segments 50 due to the reduced density or wall thickness thereof. Segments 50' and 52' can have various configurations in the expanded state, and segments 52' can be curved as shown or cylindrical.

Another manner in which the segmented configuration illustrated in FIG. 3 as well as other configurations can be obtained is by varying the cell or pore density of material 48 as disclosed in applicant's previous patent applications incorporated herein by reference. By varying the cell or pore density of material 48, the material will assume the segmented or other external configuration in the wet state, and the size of the external configuration can be increased thereafter by inflating bladder 46 with the bladder conforming to the shape of the material 48.

FIG. 4 illustrates at 60 another modification of the multifunctional device according to the present invention. Multifunctional device 60 is similar to multifunctional device 10 except that multifunctional device 60 has a curved shape in the expanded state and is expanded mechanically with the use of a spine 70. Multifunctional device 60 includes elongate member 62 with distal portion 64 thereof made up of bladder 66, absorbent material 68 carried by bladder 66 and a spine 70 disposed in material 68. Spine 70 includes a plurality of arms 72 having a normal or open predetermined curved configuration as illustrated in FIG. 4. With material 68 in the dry state, the spine is maintained in a substantially straight or closed configuration by the dry, stiff condition of material 68 such that the device 60 has a compact, straight, rod-like configuration as shown in FIGS. 12 and 13 with arms 72 disposed close to a longitudinal axis of the device to allow introduction through the portal. Once the multifunctional device 60 is in the body, material 68 will absorb body fluids to become soft and allow spine 70 to return to its normal or open configuration with the angle defined by arms 72 with a longitudinal axis of the device increased or changed from the angle defined by the arms with the axis in the dry state, thusly producing a predetermined configuration, such as the elongate, curved configuration illustrated, for use in specific procedures.

Use of multifunctional device 60 is illustrated in FIG. 12 wherein the device is shown prior to being passed through a sleeve 61 that extends through the skin and muscle of the abdomen 63. Prior to being passed through sleeve 61, material 68 is rigid or stiff in the dry state with a rod-like configuration, and arms 72 are held close to the longitudinal axis due to the rigidity of material 68. In FIG. 13, device 60 has been passed through sleeve 61 and positioned with distal portion 64 disposed between the gall bladder 65 and the bowel 67. The device is shown in FIG. 13 after absorption of body fluids by material 68 with the device in the expanded state with material 68 soft, pliant and expandable and arms 72 disposed outwardly of the longitudinal axis to expand bladder 62. By making the arms 72 resilient or flexible, such as with the use of a spring material, the external size of distal portion 64 can thereafter be selectively increased by supplying fluid to the interior of bladder 66 in excess of that required to fill the bladder when the spine is open. Spine 70 can be made tubular, and arms 72 can be provided with a plurality of apertures 74 allowing substances to be introduced at the anatomical cavity or removed therefrom through the spine 70 and a tube or trunk 76 connected therewith and extending through elongate member 62.

The spine can be made to assume a predetermined configuration upon absorption of fluids by material 68 and can be utilized to expand the bladder mechanically. The spine can be disposed around or within material 64 or between material 64 and the bladder, and the spine can be disposed externally or internally of the bladder. Use of a tubular spine allows substances to be introduced at and/or aspirated or drained from the operative site and the material through the spine. With the use of a spine, the rigidity of the multifunctional device in the expanded state is increased thusly enhancing the ability of the device to move, retract and position tissue. Fluid can be withdrawn from material 68 via suction provided at tube 76 to facilitate collapse of the spine when withdrawing the device through the portal.

A multifunctional device 80 having a conical shape in the expanded state is illustrated in FIG. 5 and includes elongate member 82 having distal portion 84 made up of bladder 86, absorbent material 88 carried by bladder 86 and spine 90 disposed around material 88. Spine 90 includes a trunk 92 extending through elongate member 82 and a plurality of angularly extending branches 94 with apertures 96 therein extending from trunk 92 in a circular arrangement. Spine 90 is shown as being entirely tubular; however, it will be appreciated that the spine can have a completely tubular, solid or partly tubular configuration. The arrangement of the branches 94 when the material 88 is in the wet state can have any desired configuration in addition to the circular arrangement shown in FIG. 5. In the dry state for material 88, the branches 94 are maintained in a closed or collapsed or substantially collapsed condition due to the rigidity of the material 88, and the branches assume the predetermined open configuration upon absorption of body fluids by material 88. In the open configuration, the angle defined by branches 94 with a longitudinal axis of the device is greater than the angle defined by the branches with the axis in the collapsed condition. With the use of a branched spine, the multifunctional device can be configured as particularly desired to gently engage tissue and organ structure to properly manipulate and position the tissue and organ structure for a particular procedure. By making the branches resilient or flexible, the external size of the multifunctional device 80 can be substantially increased once the spine is open by expanding bladder 86 with fluid. By making the spine of electrically conductive material, an electrosurgical probe can be passed through the trunk 92 such that a unipolar electrosurgical device is produced with multiple electrodes along the periphery of material 88 for coagulation of large surface areas such as cystic cavities or the endometrium of the uterus. It will be appreciated that the material 88 can be disposed within the spine as shown, around the spine or the spine can be disposed within the body of material. It will be further appreciated that the spine can be disposed around the bladder 86 as shown or within the bladder as shown at 86'.

An additional modification of a multifunctional device according to the present invention is illustrated at 110 in FIG. 6. Multifunctional device 110 is similar to multifunctional device 10 except that multifunctional device 110 is expanded mechanically with the use of an expanding mechanism 125. Multifunctional device 110 includes an outer elongate tubular member 112 and an inner elongate member 113 disposed within outer member 112. Outer member 112 has a proximal end 114 secured to a hand grip 115 and a distal end 117 connected to expanding mechanism 125. Inner member 113 can be solid, partly solid, hollow or tubular and has a proximal end 119 extending proximally of the outer member proximal end 114 and joined to a hand grip 121 disposed proximally of hand grip 115. A distal end 123 of inner member 113 extends distally of outer member distal end 117 and is connected with the expanding mechanism 125 as illustrated in FIG. 7. Expanding mechanism 125 includes an arrangement of links 127 and 127' and 129 and 129'. Links 127 and 127' are pivotally connected at their ends at joints 131 and 131', respectively, to outer member distal end 117, the links 127 and 127' being disposed on opposite sides of the outer member with joints 131 and 131' in lateral alignment with each other and with a longitudinal axis of multifunctional device 110. The opposite ends of links 127 and 127' are pivotally connected to ends of links 129 and 129' at joints 133 and 133'. The opposite ends of links 129 and 129' are pivotally connected to the inner member distal end 123 at a joint 135 longitudinally aligned with joints 131 and 131'. Expanding mechanism 125 is disposed within bladder 122 which is sealed to the distal end 117 of outer member 112, and a layer or body of absorbent material 124 can be carried by the bladder. Expanding mechanism 125 is normally disposed in a closed or collapsed position as illustrated in FIG. 6 with links 127 and 127' longitudinally aligned with links 129 and 129', respectively, and joints 133 and 133' laterally aligned with each other and with the longitudinal axis to form a substantially straight, linear, rod-like arrangement facilitating introduction through the portal. A handle 137 for actuating expanding mechanism 125 includes hand grips 115 and 121, a spring member 139 connecting hand grips 115 and 121 and a locking mechanism 141 for fixing the relative position of the hand grips. The hand grips 115 and 121 and the spring member 139 can be made unitarily, integrally as one piece as shown or the spring member can be made separately from the hand grips and secured thereto. Manipulating rings 143 can be provided on hand grips 115 and 121 to facilitate relative displacement of the hand grips via manual squeezing and spreading actions as will be explained further below. The hand grips can be permanently or releasably connected to the proximal ends of the outer and inner members, respectively. The locking mechanism 141 includes a locking arm 145 pivotally connected to hand grip 121 and having a plurality of angular projections 147 therealong or other detents for cooperating with a slot 149 in hand grip 115. Slot 149 can be configured to cooperate with projections 147 to lock arm 145 therein or the slot can be provided with other retaining structure or means for locking or holding the arm. A lever 151 can be provided at the free end of locking arm 145 for moving the locking arm relative to slot 149 to release the detents. The proximal end 119 of inner member 113 can be connected with a stop cock 134 to control the supply and release of fluid through the inner member 113 for additional expansion and contraction of bladder 122 via the inner member where the inner member is hollow, tubular or formed with an internal channel.

In use, multifunctional device 110 is introduced at an internal operative site with expanding mechanism 125 in the normally closed or collapsed position and bladder 122 in the contracted state with hand grips 115 and 121 in an initial position as illustrated in FIG. 6. When it is desired to expand device 110, hand grips 115 and 121 are manually spread or moved apart via manipulating rings 137 from the initial position causing the outer and inner members to move relative to one another. In response to relative movement of the outer and inner members via spreading operation of handle 137, expanding mechanism 125 will be moved to an open position to expand bladder 122 as illustrated in FIG. 8. Expanding mechanism 125 is shown in FIG. 8 as being in a fully open position with joints 133, 133' and 135 in alignment in a direction transverse or perpendicular to the longitudinal axis such that the links are disposed at an angle with the longitudinal axis to define a triangular configuration with bladder 122 conforming to the configuration of the links, the triangular configuration of FIG. 8 being particularly useful for uterine manipulation. The expanding mechanism 125 will be locked in the fully open position due to projections 147 being held in slot 149, and the projections allow controlled, incremental expansion of bladder 122. Expanding mechanism 125 can be moved to various intermediate open positions to control or vary the external size as well as the configuration of device 110 in the expanded state in accordance with the amount of relative displacement of hand grips 115 and 121. For example, device 110 is shown in FIG. 9 in a second expanded state with expanding mechanism 125 in a partially open position to form a quadrilateral configuration symmetrical around the longitudinal axis. In the partially open position of FIG. 9, joints 133 and 133' are disposed proximally of joint 135 and are disposed outwardly of the longitudinal axis in alignment in a direction transverse thereto. Where it is desired to supply fluid to bladder 122 for additional expansion, the inner member 113 can be connected with a source of fluid. When additional expansion is not desired, the bladder can be provided with apertures allowing various substances to be supplied to the anatomical cavity or for drainage through the inner member. When it is desired to contract device 110, lever 151 is utilized to move or pivot arm 145 to release projections 147 from slot 149 allowing the hand grips 115 and 121 to be returned automatically to the initial position by spring 139 thusly closing expanding mechanism 125. It will be appreciated that spring 139 need not be provided and that the hand grips 115 and 121 can be manually squeezed to move the inner and outer members relative to one another to close the expanding mechanism.

The expanding mechanism can be made in many various ways in addition to the linkage arrangement shown. For example, the expanding mechanism can be made flexible or resilient, such as wholly or partially of spring material, and can be made integrally, unitarily as one piece or as separate pieces. Where the expanding mechanism is made as an arrangement of links or hinges, the links can be made of spring material or a non-spring material, and the joints can be pre-loaded to bias the expanding mechanism to the open position. FIG. 10 illustrates a pre-loaded joint 135' for use with the expanding mechanism 125, the joint 135' including a torsion spring 153 secured to link 129 and to inner member 113 to bias link 129 to rotate in a clockwise direction around pivot 155. With the use of torsion springs or other bias devices or by forming the expanding mechanism of spring material, various orientations and configurations for the expanding mechanism in the open position can be obtained. Where the expanding mechanism is biased to the open position, the rigidity or stiffness of material 124 in the dry state can be utilized to maintain the expanding mechanism in the closed position, and the expanding mechanism will automatically move to the open position upon absorption of body fluids by the material 124. Accordingly, handle 137 can be designed for squeezing operation only to close the expanding mechanism to facilitate withdrawal of the multifunctional device. Depending on the configuration of the expanding mechanism, a multifunctional device having a biased or pre-loaded expanding mechanism can also be introduced through the portal with the expanding mechanism retracted or disposed within outer member 112 to be held by the outer member in the closed position. Upon introduction of the multifunctional device at the operative site, the handle can be utilized to move the inner and outer members relative to one another to extend or uncover the expanding mechanism and permit opening thereof. It will be appreciated that the body of material can be disposed around the expanding mechanism with or without a bladder disposed around the material as illustrated at 124' and 122' in FIG. 9.

Yet another modification of a multifunctional device according to the present invention is illustrated in FIG. 11 at 210. Multifunctional device 210 is similar to multifunctional device 10 except that material 224 for multifunctional device 210 is disposed within bladder 222. Multifunctional device 210 includes elongate member 212 having a distal portion 220 made up of bladder 222 with material 224 carried therein and a proximal portion made up of a connector 257 which can be flexible, rigid and/or bendable. Connector 257 can be secured to the bladder 222 as shown, the material 224 or both. Connector 257 can be coupled with a valve or stop cock 234 having a coupling 259 for communicating with a source of fluid, such as saline, to be supplied to the interior of bladder 222. As shown in phantom at 290, a spine can be disposed in material 224, the spine 290 having a trunk 292 and a plurality of branches 294 extending angularly from trunk 292.

Operation of multifunctional device 210 is similar to that previously described in that the device is introduced at an internal operative site through a portal in the non-expanded or contracted state with the material 224 in a dry state. Where spine 290 is provided, the branches 292 are held close to a longitudinal axis of the device at a relatively small or no angle. In order to expand device 210, fluid is supplied to the interior of bladder 222 via connector 257 for absorption by material 224. In the wet state, material 224 will expand in size, thusly expanding bladder 222. Where spine 290 is provided, the branches 292 will define a greater angle with the longitudinal axis for increased rigidity and/or additional expansion of the device. Multifunctional device 210 is particularly useful for occupying space in an anatomical cavity and has the advantage of increasing the safety of endoscopic procedures in that, if bladder 222 ruptures during use of the device, such as when positioning or holding tissue or organ structure, the presence of material 224 ensures that the tissue or organ structure does not suddenly move into the operative area to be damaged by instruments thereat, obstruct visualization or otherwise impair the operative procedure, and the compliant nature of the material in the wet state ensures that the tissue or organ structure is not damaged. It will be appreciated that material 224 need not be supplied with fluid through connector 257 and that bladder 222 can contain holes or apertures allowing material 224 to absorb body fluids at the operative site. Where provided without holes or apertures, the bladder can be not secured to material 224 or secured to the material at one or more discrete locations, such as the rearward end thereof, allowing fluid in excess of that required to place material 224 in the wet state to be supplied through connector 257 for additional expansion of the bladder. Material can be removed from the bladder and the material through the connector to facilitate withdrawal of the multifunctional device.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A device for introduction into an anatomical cavity through an endoscopic portal in endoscopic procedures comprising
    an elongate member having a distal portion including a distal end for being introduced into the anatomical cavity through the portal and having a proximal portion including a proximal end for being disposed externally of the anatomical cavity;
    an expandable bladder along said distal portion;
    a body of fluid absorbing material carried by said bladder, said fluid absorbing material having a dry state prior to introduction of said distal end through. the portal and a wet state upon absorbing body fluids after introduction of said distal end into the anatomical cavity; and
    means communicating with said bladder for expanding said bladder to increase the cross sectional size of said device after said distal end is introduced through the portal into the anatomical cavity. and for contracting said bladder to decrease the cross sectional size of said device to facilitate withdrawal of said distal end through the portal, said means for expanding and contracting including mechanical means disposed within said fluid absorbing material and mechanically movable to increase and decrease the size of said device.

2. A device for introduction into an anatomical cavity through a narrow portal comprising
    an elongate member having a distal portion including a distal end for being introduced into the anatomical cavity through the portal and having a proximal portion including a proximal end for being disposed externally of the anatomical cavity;
    mechanical means along said distal portion and being movable between a first configuration and a second configuration;
    a body of fluid absorbing material disposed within said mechanical means, said fluid absorbing material having a dry state prior to introduction of said distal end through the portal and a wet state upon absorbing body fluids after introduction of said distal end into the anatomical cavity; and
    means connected with said mechanical means for moving said mechanical means to said second configuration after said distal end is introduced through the portal into the anatomical cavity and for moving said mechanical means to said first configuration to facilitate withdrawal of said distal end through the portal, said device having a first cross-sectional size when said mechanical means is in said first configuration and a second cross-sectional size greater than said first size when said mechanical means is in said second configuration.

3. A device for introduction into an anatomical cavity through a narrow portal comprising
    mechanical means movable between a first configuration and a second configuration, said device having a longitudinal axis, said mechanical means including a plurality of members connected to allow changing of the angle between said members and said longitudinal axis;
    a body of fluid absorbinq material carried by said mechanical means, said fluid absorbing material having a dry state prior to introduction through the portal and a wet state upon absorbing body fluids after introduction into the anatomical cavity; and
    means connected with said mechanical means for moving said mechanical means to said second configuration after said device is introduced through the portal into the anatomical cavity and for moving said mechanical means to said first configuration to facilitate withdrawal of said device through the portal, said device having a first cross-sectional size when said mechanical means is in said first configuration and a second cross-sectional size greater than said first size when said mechanical means is in said second configuration, said moving means connecting with said members to angularly move said members to an expanded position in said second configuration and to a compressed position in said first configuration.

4. A device as recited in claim 3 wherein said members are flexible.

5. A device as recited in claim 3 wherein said members are formed of pivotally connected links.

6. A device as recited in claim 3 and further including an expandable membrane carried by said mechanical means.

7. A device for introduction into an anatomical cavity through an endoscopic portal in endoscopic procedures comprising
    an inflatable bladder;
    a body of fluid absorbing material carried by said bladder, said fluid absorbing material having a dry state prior to introduction through the portal and a wet state upon absorbing body fluids after introduction into the anatomical cavity; and
    means communicating with said bladder for inflating said bladder to increase the external size of a portion of said device disposed within the anatomical cavity and for deflating said bladder to reduce the size of said portion to facilitate withdrawal of said device through the portal, said means for inflating and deflating including means for supplying fluid to and withdrawing fluid from said bladder.

8. A device as recited in claim 7 wherein said means for inflating and deflating includes means for supplying saline to and withdrawing saline from said bladder.

9. A device as recited in claim 7 and further including a spine for guiding said portion disposed within the anatomical cavity to assume a predetermined configuration when inflated by said inflating means.

10. A device as recited in claim 7 wherein said bladder includes a membrane with relatively elastic and inelastic portions to cause said bladder to assume a predetermined configuration when inflated by said inflating means.

* * * * *